United States Patent
Vellaisamy (10) Patent No.: US 10,585,062 B2
(45) Date of Patent: Mar. 10, 2020

(54) ELECTROCHEMICAL DETECTOR

(71) Applicant: City University of Hong Kong, Kowloon (HK)

(72) Inventor: A. L. Roy Vellaisamy, Kowloon (HK)

(73) Assignee: City University of Hong Kong, Kowloon (HK)

( * ) Notice: Subject to any disclaimer, the term of this patent is extended or adjusted under 35 U.S.C. 154(b) by 261 days.

(21) Appl. No.: 14/848,497

(22) Filed: Sep. 9, 2015

(65) Prior Publication Data

US 2017/0067844 A1   Mar. 9, 2017

(51) Int. Cl.
*G01N 27/414* (2006.01)

(52) U.S. Cl.
CPC .................. *G01N 27/414* (2013.01)

(58) Field of Classification Search
CPC .. G01N 27/27; G01N 27/414; G01N 27/4141; G01N 27/4145; G01N 27/4146; G01N 27/4148; G01N 2035/00326
See application file for complete search history.

(56) References Cited

U.S. PATENT DOCUMENTS

| | | | |
|---|---|---|---|
| 5,674,752 A | 10/1997 | Buckley | |
| 7,662,652 B2 | 2/2010 | Zhou | |
| 8,154,093 B2 | 4/2012 | Bradley | |
| 8,384,409 B2 * | 2/2013 | Kummel | G01N 27/4141 257/40 |
| 2007/0063304 A1 * | 3/2007 | Matsumoto | B82Y 10/00 257/462 |
| 2013/0084644 A1 * | 4/2013 | Wu | H01L 51/0036 436/98 |
| 2013/0164859 A1 | 6/2013 | Johnson | |
| 2013/0204107 A1 * | 8/2013 | Lee | A61B 5/14735 600/345 |
| 2014/0273259 A1 | 9/2014 | Friedman | |
| 2016/0155948 A1 * | 6/2016 | Murase | B82Y 15/00 422/69 |
| 2017/0110678 A1 * | 4/2017 | Zang | H01L 51/0554 |

FOREIGN PATENT DOCUMENTS

WO      2013081684 A3    6/2013
WO   WO 2015012186 A1 *  1/2015 ............. B82Y 15/00

* cited by examiner

*Primary Examiner* — Mayla Gonzalez Ramos
(74) *Attorney, Agent, or Firm* — Renner Kenner Greive Bobak Taylor & Weber (57) ABSTRACT

A system and method for an electrochemical detector includes a plurality of receptors disposed on a semiconductor layer, wherein the plurality of receptors are arranged to interact with a target substance so as to alter an electrical characteristic of the semiconductor layer.

19 Claims, 5 Drawing Sheets

ELECTROCHEMICAL DETECTOR

TECHNICAL FIELD

The present invention relates to an electrochemical detector, for use in a communication system, although not exclusively, to an electrochemical detector for detecting chemicals in liquid and/or vapour phases.

BACKGROUND

Pollution is one of the most serious public health problems in cities around the world. Various pollutants or containments in air or water may affect the health of the general public. Therefore, the quality of air and water must be regularly examined to ensure that some poisonous or hazardous pollutants do not exceed safety levels.

The concentration of these pollutants may be determined by using testing agents. The traditional chemical testing approaches are time consuming and may not response promptly. Alternatively, material characterization techniques in laboratories may be used to analyse the concentration of a target substance and even the composition of a testing sample. Although the results may be very accurate and sensitive, these techniques used in laboratories may not be suitable for daily applications which may requires prompt and low-cost testing results.

SUMMARY OF THE INVENTION

In accordance with a first aspect of the present invention, there is provided an electrochemical detector comprising a plurality of receptors disposed on a semiconductor layer, wherein the plurality of receptors are arranged to interact with a target substance so as to alter an electrical characteristic of the semiconductor layer.

In an embodiment of the first aspect, the target substance is a fluid based target.

In an embodiment of the first aspect, the target substance is a vapour based target or a liquid based target.

In an embodiment of the first aspect, the plurality of receptors includes at least one functionalized receptor.

In an embodiment of the first aspect, the plurality of receptors are arranged to interact with the target substance by forming chemical bonds with the target substance.

In an embodiment of the first aspect, an interaction between the plurality of receptors and the target substance is a hydrogen bonding interaction.

In an embodiment of the first aspect, whereupon the plurality of receptors interacts with the target substance, a current-voltage characteristic of the semiconductor layer is altered.

In an embodiment of the first aspect, an electrical resistance of the semiconductor layer is altered.

In an embodiment of the first aspect, the semiconductor layer includes at least one of an organic semiconductor, a polymer semiconductor, small molecules, an oxide-based semiconductor and a silicon-based semiconductor.

In an embodiment of the first aspect, further comprising a substrate under the semiconductor layer and at an opposite side of the plurality of receptors disposed.

In an embodiment of the first aspect, the substrate is a flexible substrate.

In an embodiment of the first aspect, the substrate is a polyethylene terephthalate substrate.

In an embodiment of the first aspect, the substrate includes insulating material and/or semiconductor.

In an embodiment of the first aspect, the insulating material further includes at least one of polymer, glass and ceramic.

In an embodiment of the first aspect, further comprising at least two electrodes disposed on or above the semiconductor layer.

In an embodiment of the first aspect, the at least two electrodes include an electrical conductive material.

In an embodiment of the first aspect, the semiconductor layer, the plurality of receptors and the electrodes are based on organic materials and/or metal oxide.

In an embodiment of the first aspect, the plurality of receptors form a layer of material with a thickness of 10 nm to 200 nm.

In an embodiment of the first aspect, the semiconductor layer has a thickness of 10 nm to 200 nm.

In an embodiment of the first aspect, the at least two electrodes are spaced at a distance in a range of around 50 µm to 1000 µm.

In accordance with a second aspect of the present invention, there is provided a method of fabricating an electrochemical detector in accordance with the first aspect, comprising the steps of:
  depositing the semiconductor layer on a substrate; and
  depositing the plurality of receptors on the semiconductor layer.

In an embodiment of the second aspect, the step of depositing the plurality of receptors on the semiconductor layer comprise the steps of dissolving the plurality of receptors in a solvent and depositing the plurality of receptors dissolved in the solvent on the semiconductor layer.

In an embodiment of the second aspect, the step of depositing the plurality of receptors on the semiconductor layer comprise the steps of physical vapour deposition (PVD) or chemical vapour deposition (CVD) on the semiconductor layer.

In an embodiment of the second aspect, further comprising the step of depositing a layer of electrical conductive material defining at least one electrode on or above the semiconductor layer.

In an embodiment of the second aspect, the steps of depositing the semiconductor layer, and/or the plurality of receptors and/or the layer of electrical conductive material involve a solution process.

In an embodiment of the second aspect, the solution process involves spin coating and/or printing.

In an embodiment of the second aspect, the solution process of printing further includes pad printing and/or silk screening.

In accordance with a first aspect of the present invention, there is provided a method of detecting a target substance, comprising the steps of:
  exposing an electrochemical detector in accordance with the first aspect to the target substance;
  applying a voltage and/or a current bias across the at least two electrodes; and
  determining an amount of target substance detected based on a current-voltage characteristic of the electrochemical detector exposed to the target substance.

In an embodiment of the third aspect, the step of determining an amount of target substance detected based on the current-voltage characteristic of the electrochemical detector exposed to the target substance includes determining a change of electrical impedance across the at least two electrodes of the electrochemical detector.

BRIEF DESCRIPTION OF THE DRAWINGS

Embodiments of the present invention will now be described, by way of example, with reference to the accompanying drawings in which.

DETAILED DESCRIPTION OF THE PREFERRED EMBODIMENT

The inventors have, through their own research, trials and experiments, devised that the detection of chemicals in vapour/liquid phase such as contaminants in water is of particular interest due to their importance in areas ranging from environment protection to quality control of food products. Traditional methods of detection include Ion Mobility Spectrometry (IMS) and its products, Surface Acoustic Wave (SAW) sensing technology and its products, Cantilever based sensing technology, Surface Enhanced Raman Scattering (SERS) technology, Molecularly imprinted polymer sensing technology etc. However, most of these methods are not good candidates for use in daily applications where cheap and disposable sensors are necessary.

Thin film based sensors have high sensitivity and selectivity, which require only simple device fabrication process. In addition, thin film devices have may be printed in large areas to reduce the fabrication cost.

Figure 1:
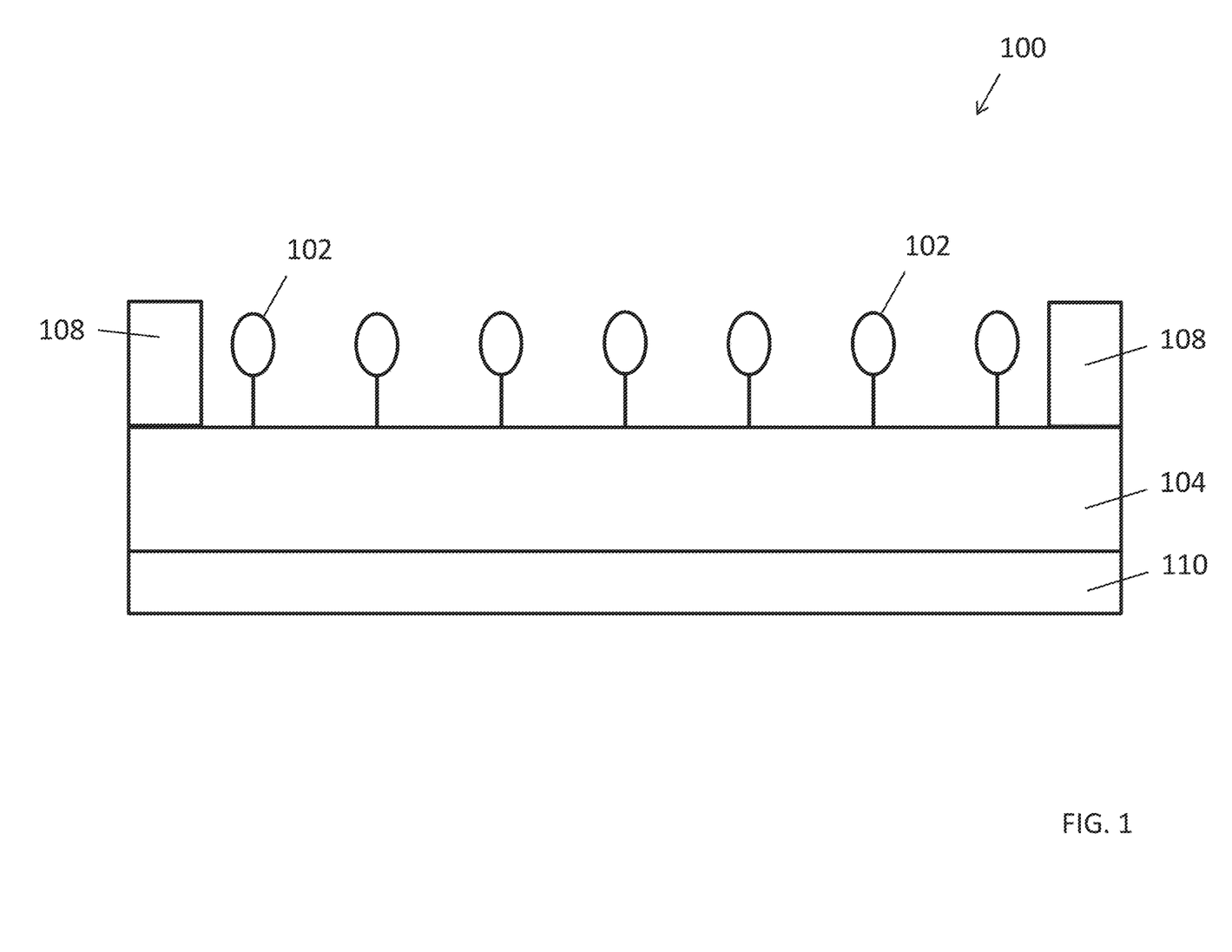
FIG. 1 is a side view of an electrochemical detector in accordance with one embodiment of the present invention.

With reference to FIG. 1, there is shown an example embodiment of an electrochemical detector 100 comprising a plurality of receptors 102 disposed on a semiconductor layer 104, wherein the plurality of receptors 102 are arranged to interact with a target substance 106 so as to alter an electrical characteristic of the semiconductor layer 104.

In this embodiment, the electrochemical detector 100 comprises receptors 102 such as chemical receptors arranged to interact with other chemical substances when exposed in a testing environment. For example, a gaseous target substance 106 may be found in air such that the receptors 102 may interact with the gaseous target substances 106 in air when the electrochemical detector 100 is placed in air. Alternatively, a liquid based target substance 106 may be applied on the electrochemical detector 100 such that the receptors 102 may contact with the target substance 106 and subsequently interact with the target substance 106.

Preferably, the receptors 102 may include at least one functionalized receptor or a functional group, and the receptors 102 may interact with the target substance 106 by reacting chemically with the target substance 106, such as forming chemical bonds with the target substance 106. This interaction may also include a hydrogen bonding interaction in which the receptors 102 may form hydrogen bonds with the target substances 106. Alternatively, the receptors 102 may react and/or interact with the target substances 106 in form of other reactions and/or interactions.

The electrochemical detector 100 also comprises a semiconductor layer 104. The semiconductor layer 104 has a unique electrical characteristics which allows/disallows electric current or electrons to pass through under different conditions. For example, the semiconductor may be arranged to allow electric current to pass through when a target substance 106 is detected and/or to disallow electric current to pass through when the concentration of the target substance 106 is below a predetermined value.

The semiconductor layer 104 includes different semiconductor material, such as an organic semiconductor, a polymer semiconductor, small molecules, an oxide-based semiconductor and/or a silicon-based semiconductor. Different semiconductor material may be selected for different fabrication processes, matching with the substrate layer and/or the receptors 102, or other factors such as required performance such as sensitivity, response time, detection range, etc.

To facilitate the measurement of an electric current passing through the semiconductor layer 104, the electrochemical detector 100 may comprise two electrodes 108 on or above the semiconductor layer 104. The electrodes 108 may be deposited directly on the semiconductor layer 104 and contact with the semiconductor layer 104 which may enhance the electrical conductivity at the electrode-to-semiconductor interface. Alternatively, the electrodes 108 may be deposited on the layer of material including the plurality of receptors 102 in some device structures. These different structures may result in different electrode-to-semiconductor contact resistances, since the receptor layer between the electrode 108 and the semiconductor layer 104 may effectively enhance or degrade the conductivity at the interfaces between different layers.

One or more electrodes 108 may be deposited on or above the semiconductor layer 104 to facilitate the measurement. The electrodes 108 may include one or more metal pads defined on or above the semiconductor layer 104. Alternatively, the electrodes 108 may include any electrically conductive material such as but not limited a metal, a doped semiconductor, or a conductive oxide.

The electrochemical detector 100 may be fabricated on a substrate 110, as shown in FIG. 1, the substrate 110 is substantially under the semiconductor layer 104 and at an opposite side of the plurality of receptors 102 disposed. The substrate 110 may consist of a material which provides additional mechanical strength to the entire structure of the electrochemical detector 100. For example, this may include a material such as a polymer, glass or ceramic. The substrate 110 may be a flexible substrate 110 such as a polyethylene terephthalate (PET) substrate, or alternatively a non-flexible substrate in some other structures. In some example embodiments, the substrate 110 is the semiconductor layer 104 (such as a silicon substrate), which includes a necessary stiffness for supporting the entire structure of the electrochemical detector 100 as well as the required semiconductor material with the desired electrical properties.

Optionally, all the deposited layers of material of the electrochemical detector 100, including the layer of receptors 102, the semiconductor layer 104 and the electrodes 108 are based on organic material. This may be advantageous for some preferred fabrication processes which may only requires low-temperature processes and/or solution process, such that the fabrication complexity and cost may be kept low.

Figure 2:
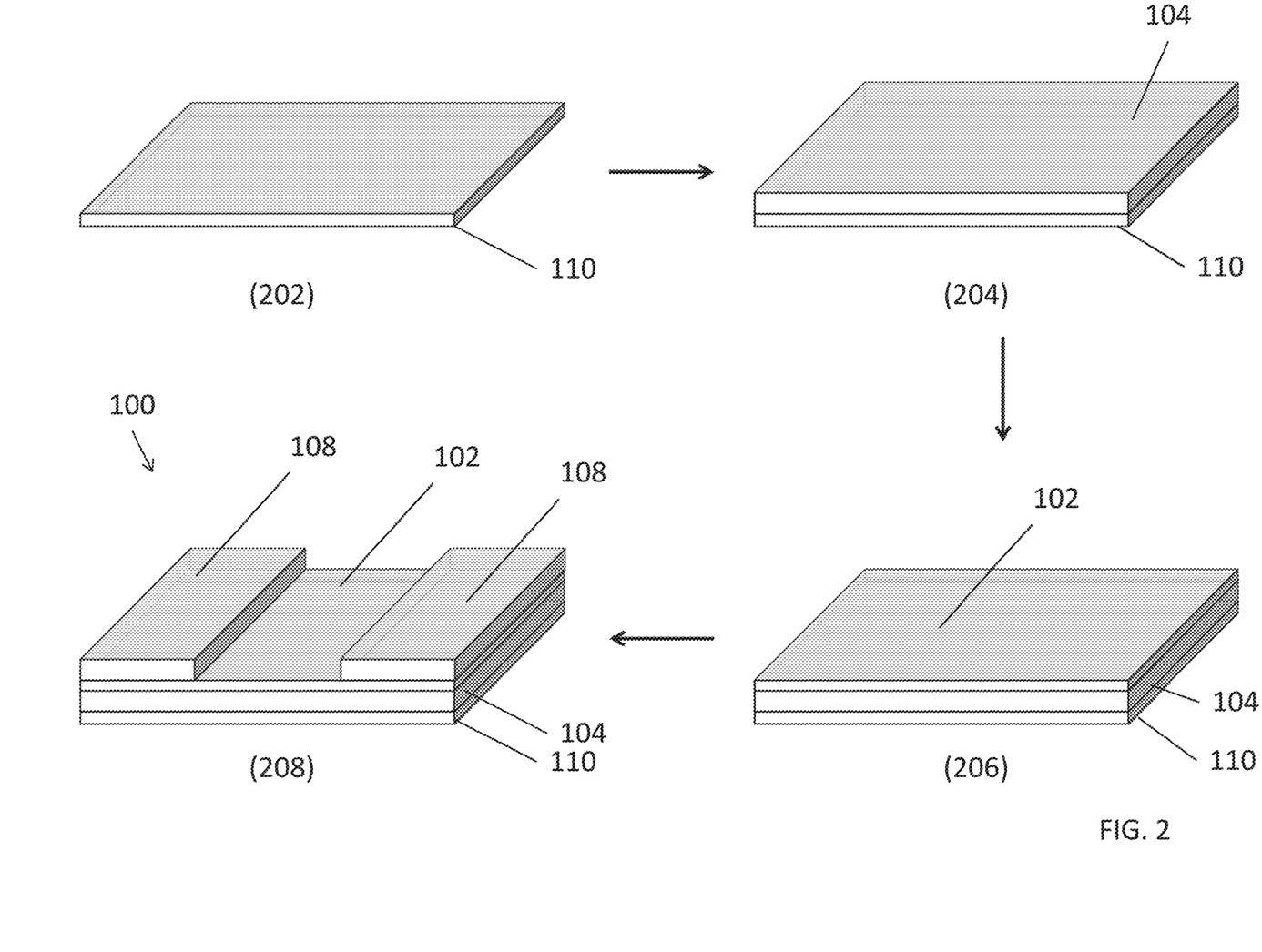
FIG. 2 is an illustration showing a process flow of a fabrication of the electrochemical detector of FIG. 1.

With reference to FIG. 2, the fabrication of the electrochemical detector 100 may comprise four main steps or processes. Firstly, at step 202, a substrate 110 such as a flexible PET substrate is cleaned according to a standing cleaning procedure. Secondly, at step 204, the semiconductor layer 104 is deposited on the substrate 110. For example, organic based semiconductor material may be spin coated or printed on the PET substrate, followed by drying the deposited solution to form a thin film of semiconductor. Thirdly, at step 206, a plurality of functionalized receptors 102 are dissolved in a solvent, such as but not limited to water, acetone, acetonitrile, methanol, ethanol, propanol, butanol, ethyl acetate, ethylene glycol, benzene, chloroform, tetrahydrofuran, t-butyl alcohol, cyclohexane, chloroethane, diethyl ether, diethyl glycol, dimethyl sulfoxide or any other solvent suitable for dissolving the plurality of functionalized receptors 102. Subsequently, the receptors 102 and the solvent is spin coated or printed on the surface of the deposited semiconductor layer 104. The solvent may then be driven away in a following drying process so as to form a layer of material comprising the receptors 102.

Alternatively, the plurality of receptors 102 on the semiconductor layer 104 may be deposited using physical vapour deposition (PVD) or chemical vapour deposition (CVD) on the semiconductor layer 104.

In this example, the thickness of the semiconductor layer 104 is about 50 nm and the layer of receptors 102 is about 30 nm. These thickness values may vary in different designs so as to optimize a number of parameters such as any process variations, the electrical resistance value of the semiconductor layer 104 and/or the layer of receptors 102, the contact resistance between the electrodes 108 and the semiconductor, the field-effect introduced to the semiconductor layer 104 when the receptors 102 interact with the target substance 106s, etc.

Finally, at step 208, two electrodes 108 such as copper metal films or other conductive material are deposited on the surface of the receptors 102. In an alternative embodiment, the layer of receptors 102 may be patterned such that electrodes 108 may contact directly with the semiconductor layer 104. The electrodes 108 may be deposited by conformal deposition of a layer of conductive material using spin coating and/or printing followed by a subsequent patterning of the layer of conductive material. Alternatively, the electrodes 108 may be patterned when it is deposited on or above the semiconductor layer 104 using any printing techniques.

Preferably, the at least two electrodes 108 are spaced at a distance in a range of around 50 μm 100 μm. This effectively affects the area of the receptors 102 exposed to and interacting with the target substance 106, and the electrical resistance of the semiconductor and/or the layer of receptor material between the two electrodes 108. These parameters in turns affect the sensitivity and performance of the electrochemical detector 100.

Preferably, the entire fabrication process is based on solution processes (such as spin coating and/or printing), and each of the deposited layers is organic material based. This allows the scale of the fabrication of the electrochemical detector 100 to be scaled up easily, such as using a roll-to-roll fabrication process with various printing technologies. These solution processes may only require low-temperature equipment and does not involve any vacuum processes which further minimize the cost of the fabrication of the electrochemical detector 100.

Figure 3:
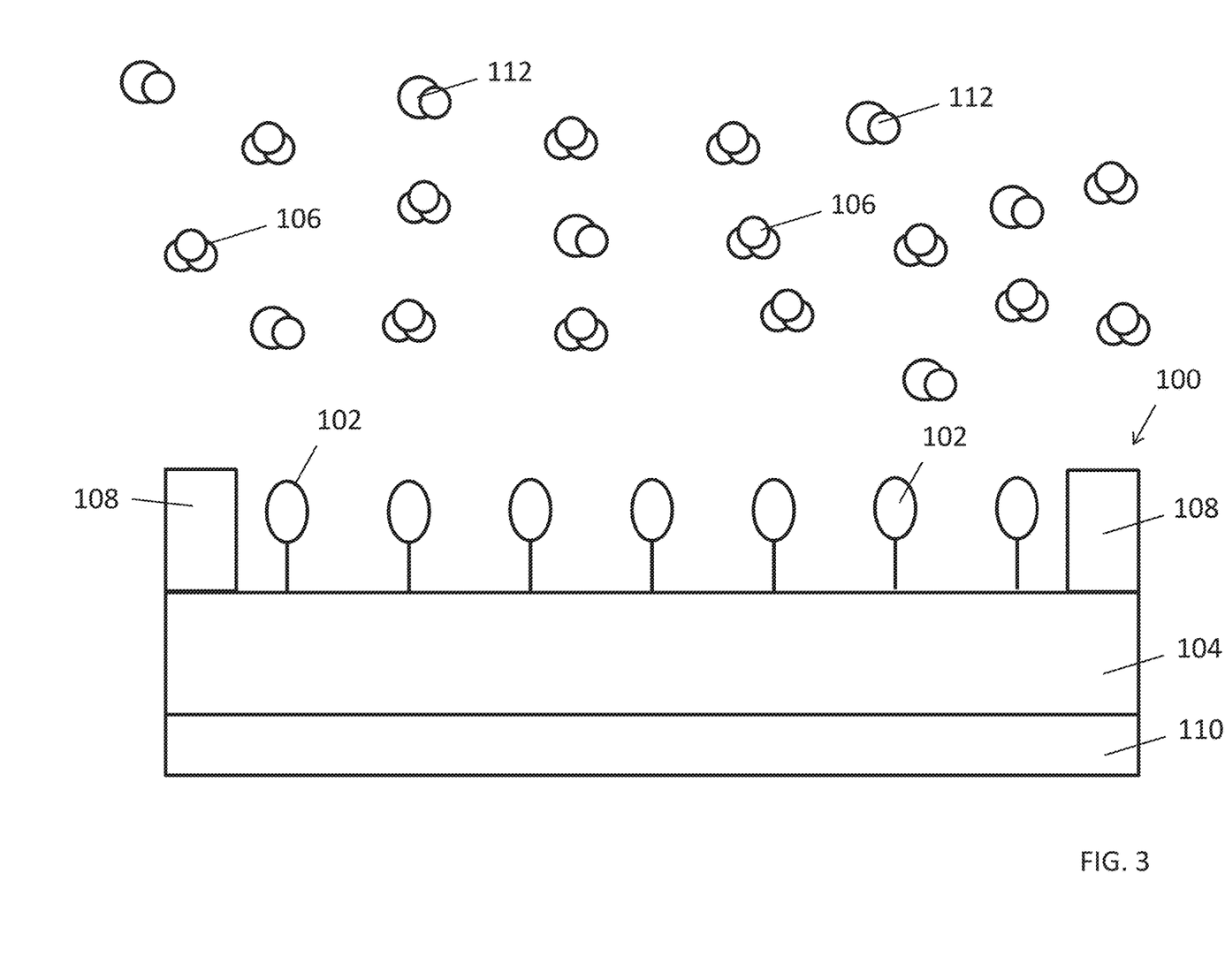
FIG. 3 is an illustration of an electrochemical detector of FIG. 1 exposed to a target substance.
Figure 4:
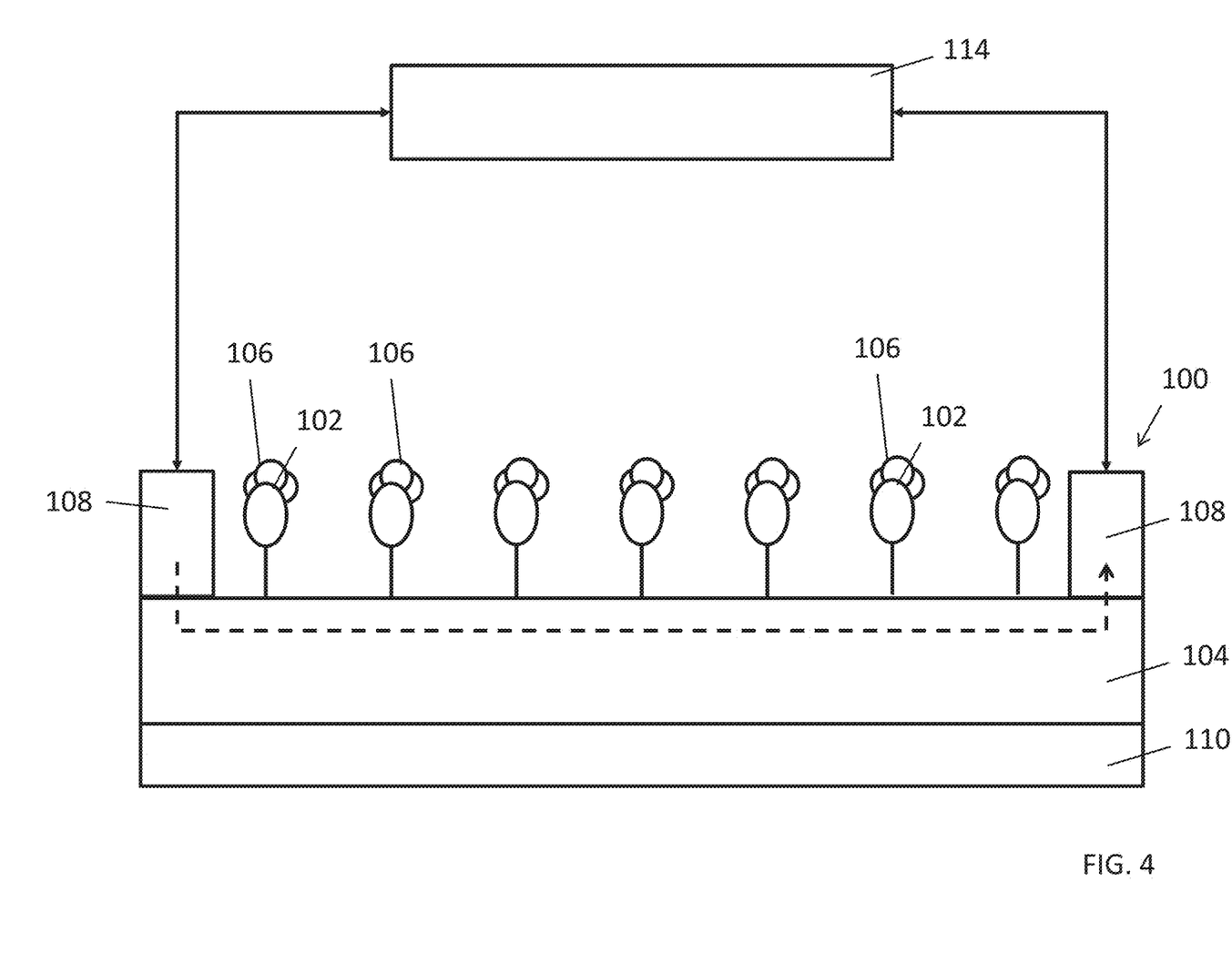
FIG. 4 is an illustration of detecting a target substance by using the electrochemical detector of FIG. 1.

With reference to FIGS. 3 to 4, there is shown an example of detecting a target substance 106 using an electrochemical detector 100. In this example, an electrochemical detector 100 is exposed to the target substance 106. By applying a voltage or a current bias across the two electrodes 108, the current-voltage characteristic of the electrochemical detector 100 under the influence of target substance 106 can be obtained. Different amount or concentration of the target substance 106 may then be determined based on the different current-voltage characteristic obtained. In some examples, the current-voltage characteristic may be characterized as an electrical resistance value across the two electrodes 108, which means that the amount of target substance 106 detected is represented by the change of resistance of the electrochemical detector 100.

Preferably, the target substance 106 is a fluid based target, and preferably a vapour based target or a liquid based target. The target substance 106 may be applied to the area with the plurality of receptors 102 exposed, for example a target substance 106 containing gas may be brought to the receptors 102, a target substance 106 containing solution may be dropped to contact directly with the receptors 102, or the electrochemical detector 100 may be placed in an ambient surrounded by the target substance 106 in a gas or a liquid.

As shown in FIGS. 3 and 4, the plurality of receptors 102 may only selectively interact with the target substance 106, i.e. forming chemical bonds with the target substance 106 but not any other substances 112. Whereupon the receptors 102 interact with the target substance 106, the receptors 102 temporally or permanently bond with the target substance 106 which may effectively change the electrical charging states of the receptors 102 and/or the layer of receptors 102. As a result, the current-voltage characteristic of the semiconductor layer 104 underneath may be altered, this may include a change of conductivity of the semiconductor layer 104 due to the changed electric field of the adjacent layer of receptor and/or the conductivity of the layer of receptors 102, hence the electrical resistance across the semiconductor layer 104 and/or the plurality of receptors 102 between the two electrodes 108 are altered. By using suitable measurement apparatus such as an electrical multimeter 114 or a semiconductor parameter analyser, the electrical characteristic of the electrochemical detector 100 may be determined.

These embodiments are advantageous in that the active layer of the electrochemical detector only includes two layers of material, such that the structure and hence the fabrication of the detector is kept simple, which enhance the yield and stability of the performance of the fabricated detectors. The thin film structure also minimizes the required amount to fabricate the electrochemical detector. In addition, the fabrication only requires low-cost materials and processing techniques such that large scale fabrication process is favourable.

As an example, the embodiments may be implemented as a portable drug detector. This may be used as an alcohol detector. A wide range of appropriate receptors which may be included in the electrochemical detector, this enable the electrochemical detector may be used for the detection of a wide range of target substances. Since the detection is based on selective bonding interaction between the functionalized receptors and the target substances, the detector may be used to detect extremely low levels or concentrations (down to ppb level) of target chemicals. This also enable the electrochemical detector may be used for gas leak detector.

For example, 2-aminopyridine N-oxide may be selected as the functional receptors in the previous discussed embodiments, such that the electrochemical detector may be used as a drug detector for detecting ketamine (2-(2-chlorophenyl)-2-(methylamino)cyclohexan-1-one), as ketamine may attach to 2-aminopyridine N-oxide with hydrogen bonds. It will be appreciated by a skill person that other functional receptors may be chosen so as to detect ketamine and/or other target chemicals according to different applications.

Figure 5:
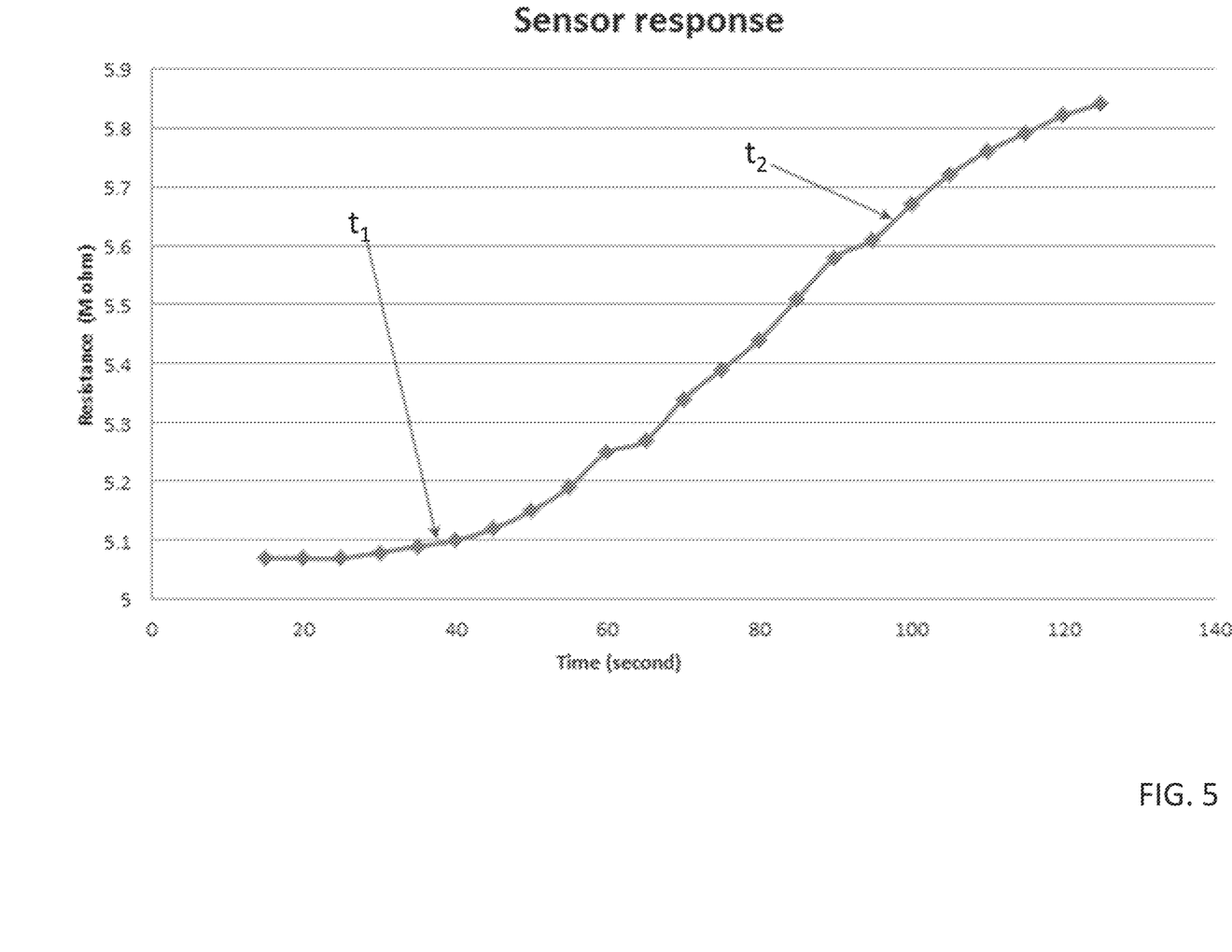
FIG. 5 is a plot showing a response of electrochemical detector of FIG. 1 exposed to a target substance.

With reference to FIG. 5, there is shown a plot showing a response of the electrochemical detector in accordance with the embodiments of the invention. The experimental setup is similar to the example as shown in FIG. 4. At $t_1$, drug was added to the testing environment, subsequently the concentration of the drug added is increased at a 1-ppb-interval. At $t_2$, 10 times of drugs were added to the testing environment. The plot shows a reasonable linear relation between the concentrations of drugs in the testing environment and the resistance values obtained using the electrochemical detector.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

The invention claimed is:

1. An electrochemical detector comprising:
a plurality of receptors of 2-aminopyridine N-oxide disposed on a single semiconductor layer;
a pair of electrodes, each electrode is disposed on and in contact with the single semiconductor layer thereby forming a two-terminal device, and the electrodes are spaced at a distance defining a resistive current path therebetween through the semiconductor layer; and
a flexible polyethylene terephthalate (PET) substrate disposed under and in contact with the semiconductor layer, wherein the substrate is at an opposite side of the plurality of receptors, wherein the plurality of receptors interact with a target substance of ketamine by forming hydrogen bonds with the target substance, so as to alter an electrical characteristic of the resistive current path, and wherein the electrical characteristic is an electrical resistance associated with a change of conductivity of a combination of the single semiconductor layer and the plurality of receptors bonding with the target substance between electrodes.

2. An electrochemical detector in accordance with claim 1, wherein the target substance is a fluid based target.

3. An electrochemical detector in accordance with claim 2, wherein the target substance is a vapour based target or a liquid based target.

4. An electrochemical detector in accordance with claim 1, whereupon the plurality of receptors interacts with the target substance, a current-voltage characteristic of the semiconductor layer is altered.

5. An electrochemical detector in accordance with claim 4, wherein an electrical impedance of the semiconductor layer is altered.

6. An electrochemical detector in accordance with claim 1, wherein the semiconductor layer includes at least one of an organic semiconductor, a polymer semiconductor, small molecules, an oxide-based semiconductor and a silicon-based semiconductor.

7. An electrochemical detector in accordance with claim 1, further comprising at least two electrodes disposed on or above the semiconductor layer.

8. An electrochemical detector in accordance with claim 7, wherein the electrodes includes an electrical conductive material.

9. An electrochemical detector in accordance with claim 7, wherein the semiconductor layer, the plurality of receptors and the electrodes are based on organic materials and/or metal oxide.

10. An electrochemical detector in accordance with claim 1, wherein the plurality of receptors form a layer of material with a thickness of 10 or more nm to 200 nm or less.

11. An electrochemical detector in accordance with claim 1, wherein the semiconductor layer has a thickness of 10 nm or more to 200 nm or less.

12. An electrochemical detector in accordance with claim 7, wherein the at least two electrodes are spaced at a distance in a range of from 50 µm or more to 1000 µm or less.

13. A method of fabricating an electrochemical detector in accordance with claim 1, comprising the steps of:
depositing the semiconductor layer on a substrate; and
depositing the plurality of receptors on the semiconductor layer.

14. A method of fabricating an electrochemical detector in accordance with claim 13, wherein the step of depositing the plurality of receptors on the semiconductor layer comprise the steps of dissolving the plurality of receptors in a solvent and depositing the plurality of receptors dissolved in the solvent on the semiconductor layer.

15. A method of fabricating an electrochemical detector in accordance with claim 13, further comprising the step of depositing a layer of electrical conductive material defining at least one electrode on or above the semiconductor layer.

16. A method of fabricating an electrochemical detector in accordance with claim 15, wherein the steps of depositing the semiconductor layer, the plurality of receptors and/or the layer of electrical conductive material involve a solution process.

17. A method of fabricating an electrochemical detector in accordance with claim 16, wherein the solution process involves spin coating or printing or both, wherein the solution process or printing further includes pad printing or silk screening or both.

18. A method of detecting a target substance, comprising the steps of:
exposing an electrochemical detector to the target substance, the electrochemical detector including
a plurality of receptors of 2-aminopyridine N-oxide disposed on a single semiconductor layer, wherein the plurality of receptors interact with a target substance of ketamine by forming hydrogen bonds with the target substance, so as to alter an electrical characteristic of this semiconductor layer, and
a pair of electrodes, each electrode is disposed on and in contact with the single semiconductor layer thereby forming a two-terminal device, and the electrodes are spaced at a distance defining a resistive current path therebetween through the semiconductor layer;
a flexible polyethylene terephthalate (PET) substrate disposed under and in contact with the semiconductor layer, wherein the substrate is at an opposite side of the plurality of receptors, and wherein the electrical characteristic is an electrical resistance associated with a change of conductivity of a combination of the single semiconductor layer and the plurality of receptors bonding with the target substance between the electrodes;
applying a voltage and/or a current bias across the first and second electrodes; and
determining an amount of target substance detected based on a current-voltage characteristic of the electrochemical detector exposed to the target substance.

19. A method of detecting a target substance in accordance with claim 18, wherein the step of determining an amount of target substance detected based on the current-voltage characteristic of the electrochemical detector exposed to the target substance includes determining a change of electrical resistance across the electrodes of the electrochemical detector.

* * * * *